United States Patent
Popp

(10) Patent No.: US 12,027,081 B2
(45) Date of Patent: Jul. 2, 2024

(54) MEDICAL DEVICE WITH A DISPLAY AND WITH A PROCESSING UNIT AND METHOD THEREFOR

(71) Applicant: Fresenius Medical Care Deutschland GmbH, Bad Homburg (DE)

(72) Inventor: Jochen Popp, Niederwerrn (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 17/918,436

(22) PCT Filed: Apr. 15, 2021

(86) PCT No.: PCT/EP2021/059740
§ 371 (c)(1),
(2) Date: Oct. 12, 2022

(87) PCT Pub. No.: WO2021/209534
PCT Pub. Date: Oct. 21, 2021

(65) Prior Publication Data
US 2023/0142997 A1    May 11, 2023

(30) Foreign Application Priority Data
Apr. 15, 2020    (DE) .......................... 102020204785.5

(51) Int. Cl.
*G09G 3/00* (2006.01)
*A61M 1/14* (2006.01)
(Continued)

(52) U.S. Cl.
CPC ............... *G09G 3/001* (2013.01); *A61M 1/14* (2013.01); *A61M 2205/502* (2013.01);
(Continued)

(58) Field of Classification Search
CPC ............... G09G 3/001; G09G 2340/14; G09G 2354/00; G09G 2380/08; G09G 2300/023;
(Continued)

(56) References Cited

U.S. PATENT DOCUMENTS 6,157,424 A  * 12/2000  Eichenlaub ........... G02F 1/1347
                                                             348/E13.059
2014/0015859 A1   1/2014  Kim et al.
(Continued)

FOREIGN PATENT DOCUMENTS

EP            2525580         6/2016

OTHER PUBLICATIONS

International Search Report and Written Opinion in International Appln. No. PCT/EP2021/059740, dated Jul. 19, 2021, 22 pages (with English translation).

*Primary Examiner* — Douglas M Wilson
(74) *Attorney, Agent, or Firm* — Fish & Richardson P.C.

(57) ABSTRACT

The disclosure relates to a medical device with a display and with a processing unit and method therefor. The processing unit is suitable for detecting states of one or more technical units of the medical device. The processing unit is further set up to control the display on the basis of detected states in order to output states of the medical device. The display is an autostereographic display. The processing unit, based on an evaluation of detected states, drives the display in such a way that a first state is visually highlighted with respect to a 3D representation, while a second state is visually not highlighted with respect to a 3D representation.

17 Claims, 2 Drawing Sheets

(51) Int. Cl.
*G02B 27/01* (2006.01)
*G02B 30/33* (2020.01)
*G16H 20/40* (2018.01)
*H04N 13/30* (2018.01)
*H04N 13/302* (2018.01)
*G02B 30/26* (2020.01)
*G02B 30/30* (2020.01)
*G06F 3/01* (2006.01)
*H04N 13/361* (2018.01)

(52) U.S. Cl.
CPC ........ *G02B 2027/0138* (2013.01); *G02B 2027/014* (2013.01); *G02B 30/26* (2020.01); *G02B 30/30* (2020.01); *G02B 30/33* (2020.01); *G06F 3/017* (2013.01); *G06F 2203/04101* (2013.01); *G06F 2203/04108* (2013.01); *G09G 2300/023* (2013.01); *G09G 2340/14* (2013.01); *G09G 2354/00* (2013.01); *G09G 2380/08* (2013.01); *G16H 20/40* (2018.01); *H04N 13/302* (2018.05); *H04N 13/361* (2018.05); *H04N 2013/405* (2018.05)

(58) Field of Classification Search
CPC ........ G02B 30/26; G02B 30/27; G02B 30/28; G02B 30/29; G02B 30/30; G02B 30/31; G02B 30/32; G02B 30/33; G02B 2027/0138; G02B 2027/014; G06F 3/017; G06F 2203/04101; G06F 2203/04108; H04N 13/302; H04N 13/361; H04N 2013/405; A61M 1/14; A61M 2205/502; G06T 7/55; G06T 7/586; G06T 7/593; G16H 20/40
See application file for complete search history.

(56) References Cited

U.S. PATENT DOCUMENTS

| | | |
|---|---|---|
| 2014/0282008 A1 | 9/2014 | Verard et al. |
| 2014/0343404 A1 | 11/2014 | Razzaque et al. |
| 2016/0106394 A1* | 4/2016 | Kang .................. A61B 8/465 600/437 |
| 2016/0110950 A1* | 4/2016 | Collette ............. G07F 17/3213 463/20 |
| 2017/0172695 A1* | 6/2017 | Daniel .................. A61M 1/16 |

* cited by examiner

MEDICAL DEVICE WITH A DISPLAY AND WITH A PROCESSING UNIT AND METHOD THEREFOR

CROSS-REFERENCE TO RELATED APPLICATIONS

The present application is the national stage entry of International Patent Application No. PCT/EP2021/059740, filed on Apr. 15, 2021, which claims priority to Application No. DE 102020204785.5, filed in the Federal Republic of Germany on Apr. 15, 2020, the disclosures of which are expressly incorporated herein in their entirety by reference thereto.

TECHNICAL FIELD

The disclosure relates to a medical device with a display and with a processing unit and methods therefor.

BACKGROUND

More and more sensors are being used in medical devices in general, but especially in dialysis machines, and the results of their measurements are being used to improve treatment. This is due both to general technical developments (smaller, less expensive sensors) and to increasingly differentiated demands on treatment (patient individuality).

In particular, the increasing data processing capacity of modern processors in the form of machine-supported "intelligent" data evaluation with a technical effect on the treatment processes carried out is increasingly being used in medicine. Here, even additional data that are supposedly not correlated with the treatment can be incorporated into the improvement of treatment results on the basis of advanced machine evaluation. This also promotes an increasing accumulation of sensor technology and associated data.

While in other industries the automation of feedback of advanced data analysis to devices is replacing humans as a necessary element of interaction, medical treatment devices continue to rely on human operation.

Reasons are, primarily, patient safety, the relative unpredictability of complications with highly individual patient and environmental preconditions, the high number of patient-oriented treatment options, and the psychosomatic effects of human-human interaction including traceability and trust.

Using dialysis treatments as an example, this will be explained in more detail below. In daily practice, during a typical treatment of a patient (within approximately several hours), the staff (nursing or medical staff) must intervene repeatedly, at high frequency, irregularly, mostly manually, and usually with the inclusion of additional material/equipment (e.g., consumables such as syringes, tubes, or medical technology equipment such as infusion pumps) in the course of treatment.

In addition to less time-critical (but error-prone and time-consuming) device interactions such as calibration, function testing, disposables setup/disassembly, and cleaning of the devices, the health-critical and immediate input of various physiological and machine-related data regarding the sequential treatment steps, as well as reactions to warnings/critical situations/indications/irregularities, take place between connection and disconnection of the patient from the device. For this purpose, treatment-controlling inputs to the dialysis machine are usually made directly on the machine. The most common way of doing this is to combine the information display with corresponding input options. The information display sometimes also allows treatment-relevant parameters to be displayed for monitoring and operating instructions.

For example, a multitude of information is essentially presented simultaneously, and it is difficult to distinguish relevance. Furthermore, the presentation of information in distinction to an (expected) input on a touchscreen poses a problem in human-machine interaction.

This situation gives rise to various problems, which on the one hand can lead to a delayed reaction because a relevant piece of information was not recognized in time, or on the other hand can lead to a potential incorrect entry of parameters or instructions. Both can impact the patient's well-being, but at the very least this leads to (time) efficiency being impaired from both the patient's and the medical facility's point of view.

This directly disadvantages patient safety, treatment efficiency, machine safety, efficient use of consumables, and can also increase staff overhead.

Another disadvantage is that users of such devices require a great deal of training in order to be instructed in their correct use. This time requirement is not always available.

Already without the influences of big data and related in medicine, the overloading of device operation with information is a known problem.

The known state of the art that attempts to solve this problem imposes inherent additional problems and is not up to the difficulties of the trend toward more information.

Common approaches (and resulting shortcomings) include contrasting by color (subjective coding, color blindness not addressed, lighting/display dependency, additional information provided by color legend), splitting operation into multiple (context-dependent) displays (more interaction required, more prone to input errors, unnecessary effort in routine processes/"clicking through"), and additional display of instruction manuals (even more information, additional potential for confusion of instruction/info/operation elements).

However, all these measures are not suitable for sustainably improving man-machine interaction.

Against this background, it is a task of the present disclosure to provide solutions that enable a more efficient and patient-safe operation of medical devices.

The problem is solved by a method for a medical device having a display and having a processing unit, the processing unit being suitable for detecting states of one or more technical units of the medical device, the processing unit furthermore being set up to drive the display on the basis of detected states, to output states of the medical device, characterized in that the display is an autostereographic display, and in that the processing unit, based on an evaluation of detected states, drives the display such that a first state is visually highlighted with respect to a 3D representation, while a second state is not visually highlighted with respect to a 3D representation. The method comprises the step of displaying the first state, the step of displaying the second state, and the step of obtaining user input with respect to the displayed first state.

The task is also solved by a medical device having a display and having a processing unit, the processing unit being suitable for detecting states of one or more technical units of the medical device, the processing unit furthermore being set up to drive the display on the basis of detected states, to output states of the medical device, characterized in that the display is an autostereographic display, and in that the processing unit, based on an evaluation of detected states, drives the display in such a way that a first state is visually highlighted with respect to a 3D representation, while a second state is not visually highlighted with respect to a 3D representation.

Further advantageous embodiments are the subject of the respective dependent claims, the figures and the description.

BRIEF DESCRIPTION OF THE DRAWINGS

The invention is explained in more detail below with reference to a drawing and examples of embodiments. The drawing is a schematic representation and is not to scale. The drawing does not limit the invention in any way.

It Shows.

In the following, the devices and methods will be described in more detail with reference to the figures. It should be noted that different aspects are described, each of which can be used individually or in combination. That is, any aspect can be used with different embodiments unless explicitly shown as a pure alternative.

Furthermore, for the sake of simplicity, only one entity will be referred to in the following. However, unless explicitly noted, the embodiments may also have several of the entities concerned in each case. In this respect, the use of the words "one" is to be understood only as an indication that at least one entity is used in a simple embodiment.

Insofar as methods are described below, the individual steps of a method can be arranged and/or combined in any order, unless the context explicitly indicates otherwise. Furthermore, the processes can be combined with each other, unless expressly indicated otherwise.

Data with numerical values are generally not to be understood as exact values, but also include a tolerance of +/−1% up to +/−10%.

Insofar as standards, specifications or the like are named in this application, reference is always made at least to the standards, specifications or the like applicable on the filing date. For example, if a standard/specification etc. is updated or replaced by a successor, the disclosure is also applicable thereto.

DETAILED DESCRIPTION

Various embodiments are shown in the figures.

Figure 2:
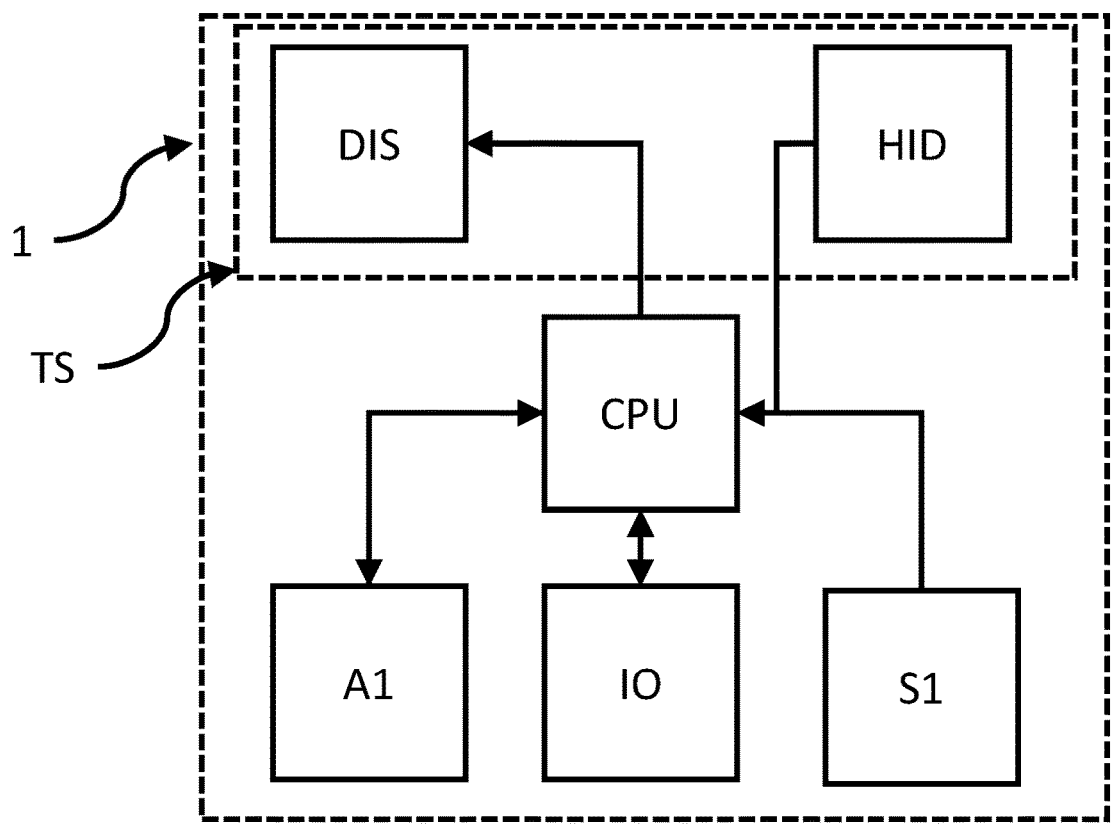
FIG. 2 is a schematic representation of elements of embodiments of a medical device.
Figure 3:
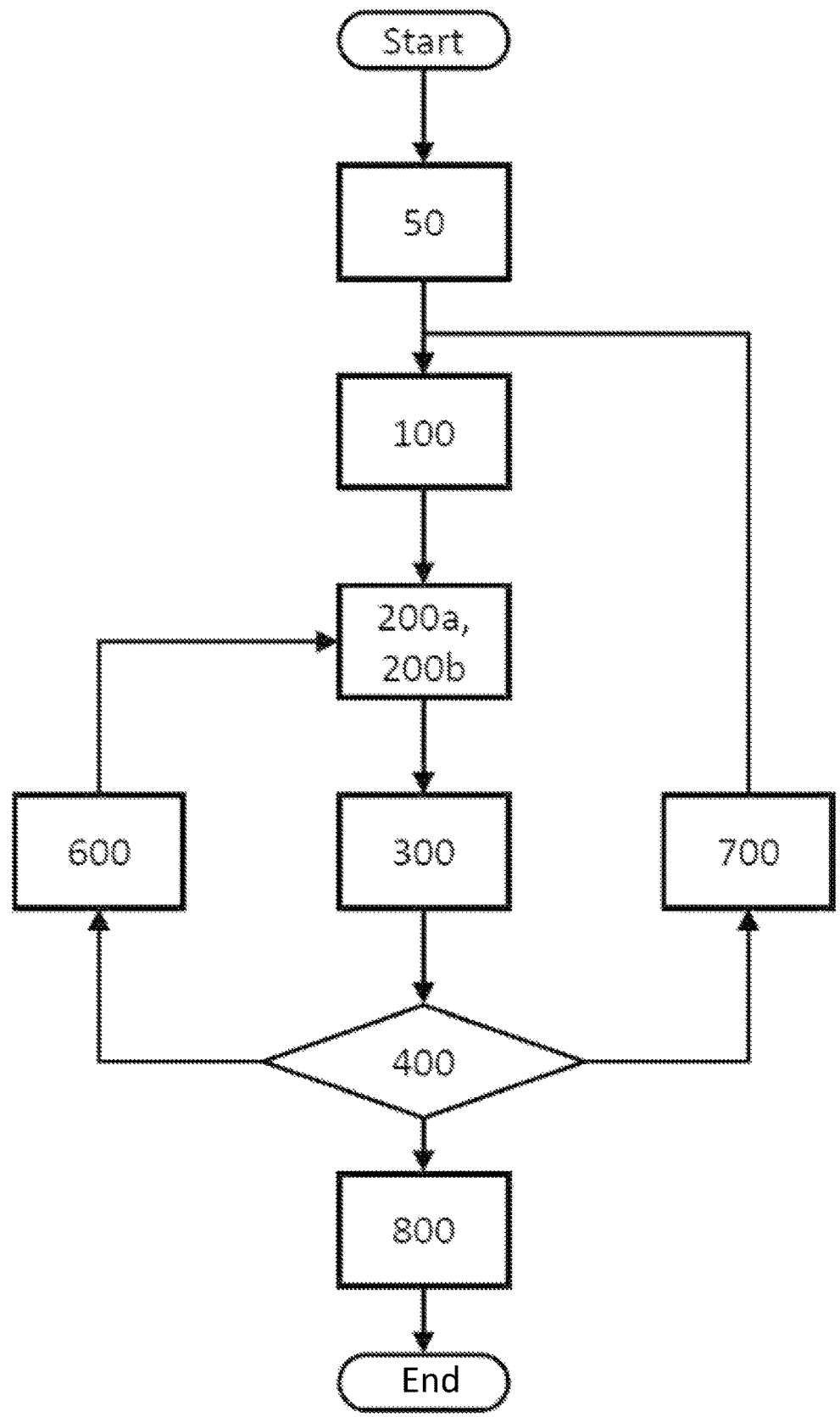
FIG. 3 is a schematic flow diagram.

In an exemplary method, a medical device 1 is used. The medical device 1 comprises, for example, a display DIS and a processing unit CPU. Furthermore, as shown in FIG. 2, further components may be integrated (as shown) or functionally connected in the medical device 1. These components include sensors S1, actuators A1, interfaces IO, input devices HID.

Sensors S1 can be, for example, sensors for determining pressure, pressure differences, temperature, pH values, concentration of certain substances in gases or liquids, volume meters, volume flow meters, etc.

Actuators A1 can be e.g. pumps, valves, elements for flow control, etc.

A processing unit CPU may comprise one or more microprocessors, microcontrollers, application-specific integrated circuit (ASIC), field programmable gate array (FPGA), etc. The processing unit may also be an arrangement of multiple units in a master-slave combination.

An input device HID may be a suitable device for recognizing input from a user U. By way of example, reference is made to an user interface of a touch screen (TS), a keyboard, a mouse, a joystick, a graphics tablet, gesture recognition (e.g. by means of a camera).

The interface IO may have a local interface for wireless/wired communication with a remote database, display and/or input unit. For example, via a near-field communication system, such as ZigBee, LAN, DECT, Bluetooth, etc., data can be transmitted. Data regarding states of sensors S1/actuators A1 can be forwarded and/or remote user input can be received by means of a remote HID.

The processing unit CPU is suitable for detecting states of one or more technical units, e.g. sensors S1 and/or states of actuators A1, of the medical device 1 in a step 100.

The processing unit CPU is further set up to control the display DIS on the basis of detected states in order to output states of the medical device 1.

The display DIS is designed as an autostereographic display. Autostereographic displays DIS allow to present three-dimensional representations to a user U without glasses.

Figure 1:
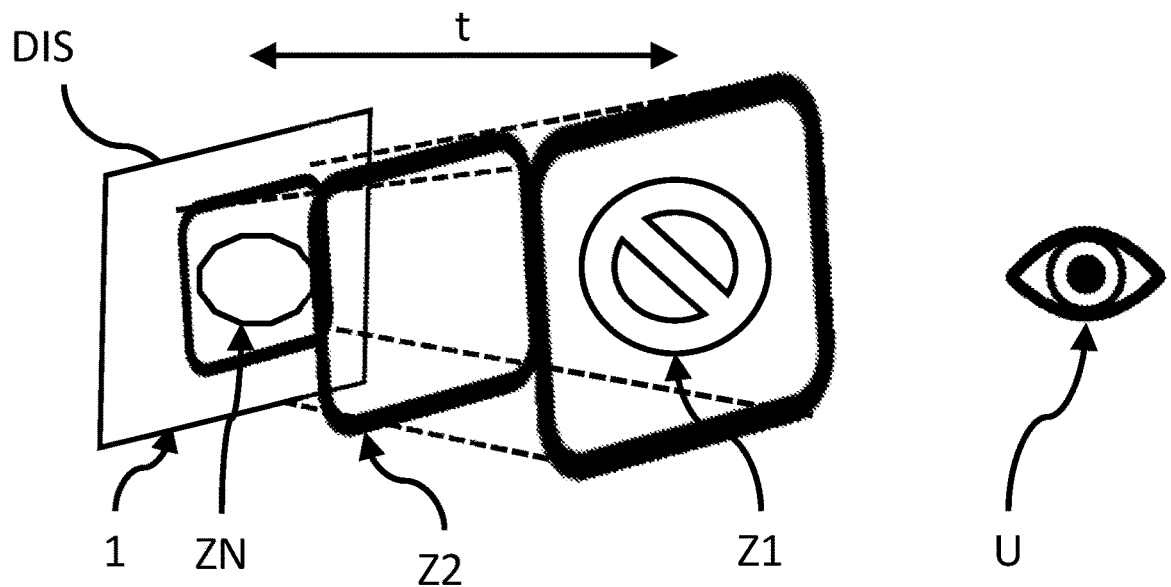
FIG. 1 is a schematic representation of state indicators with respect to a user.

The processing unit CPU can now—based on an evaluation of detected states—control the display DIS in such a way that a first state Z1 is visually highlighted with respect to a 3D representation, while a second state ZN is visually not highlighted with respect to a 3D representation, as outlined in FIG. 1.

For this purpose, the method has a step of displaying 200a the first state Z1 and a step of displaying 200b the second state ZN.

The designation as step 200a, 200b is only due to the logical distinction. I.e. the steps can also be combined in one step or executed one after the other/alternating. The processing is aligned to the hardware used.

The medical device may now receive an input from a user U, for example by means of a local input device HID or by means of an interface 10. This user input 300 relates to the displayed first state.

In one embodiment, step 100 also comprises detecting a warning or alarm message 100, wherein the detected warning or alarm message is displayed as a first state Z1 in step 200a.

For example, warnings and/or relevant interaction elements can be highlighted.

For example, in the case of critical warnings (sudden change in pressure, access needle leakage, blood in the dialyzer, etc.), to which an immediate response must be made via display input, the warning avoidance 200a can be displayed with depth effect as state Z1 and thus be set apart from the background.

In the background, parameters relevant for treatment can still be displayed in step 200b as state Z1. These other parameters may still be relevant for assessing the response.

In particular, the areas of a display DIS that need to be "touched", for example, to confirm the warning and/or to enter relevant parameter changes, can be further brought to the front even before the warning message itself.

This makes relevant interaction options directly visible, eliminates confusion with other input options, and allows potentially relevant other parameters to be viewed prior to interaction.

Because alerts can be responded to better and faster, this increases patient safety and treatment efficiency, and reduces equipment downtime due to automatic interruptions, as well as the disruption of persons due to persistent audio-visual alerts.

Without limiting generality, the first indicated state Z1 may relate to a first step of an operating procedure and the second indicated state ZN may relate to a step of the operating procedure subsequent to the first step, which are not shown separately in the flowchart. For example, in step 400, an evaluation of the input can be performed and, depending on the input, an action (e.g., relating to an actuator and/or an acknowledgement of a warning message) is performed in step 600, whereupon, for example, a state previously shown as process step ZN is now highlighted as state Z1, or the process branches in step 700 and an action (e.g. relating to an actuator and/or an acknowledgement of a warning message) is performed, whereupon the process returns to step 100. Without limiting generality, many variations can be envisioned here.

For example, a temporal sequence of operating steps/treatment steps in the spatial depth can be displayed.

The time sequence of the individual treatment processes Z1, ZN can be displayed symbolically and/or as text. The sequence can be indicated by differences in spatial depth. For example, several process steps can be displayed e.g., according to their sequence in different depths t. For example, a temporally nearer process step Z1 is represented e.g., spatially before a temporally following process step Z2 . . . ZN. Alternatively, or additionally, however, the currently running process corresponding to Z1 can be displayed in the foreground of the display DIS, while the last completed treatment steps (increasingly) corresponding to Z1 . . . ZN can continue to be displayed in the background.

Immediately pending processes can, with decreasing time remaining for execution, become progressively more prominent until they are displayed entirely in the foreground as the current process upon initiation. This can be done on different time scales (e.g., initiation-rigging-patient connection-treatment-patient separation-cleaning-functional test or within cleaning as individual cleaning steps), also displayed in parallel.

This time sequence can be displayed separately or in addition to the other display.

This enables the user to navigate in time. In particular, the user U can see the temporal relationship of the current process to the overall treatment.

Operator U is thus enabled to make preparations for upcoming treatment steps (e.g., provision of material) and to devote his attention to other patients when foreseeable risk-free processes are displayed. On the other hand, the operator U is also enabled to devote his attention to the next risky processes.

The treated patient can also adjust and prepare and/or relax for upcoming changes in treatment steps if no upcoming changes are indicated.

For example, this enables instructions for manual changes to be displayed on the medical device 1.

Particularly when setting up/breaking down consumables (tubes, dialyzers, etc.), but also in the event of irregularities during treatment, the staff must interact manually with components of the medical device 1. This is instructed and assisted on the autostereographic display DIS by 3D display of the affected parts as state Z1 (e.g., in contrast to the 2D display of the entire machine/non-relevant parts corresponding to state ZN).

Since the instructed actions on the medical device 1 do not usually take place over a wide area, but also extend to the depth of the room (laying tubing from one side to the other, opening a clamp around a tube, shaking the dialyzer, etc.), correct performance can be ensured by imitating the indicated action instruction without pretraining.

This enables such actions to be performed by inexperienced staff or—e.g., in home care—by the patient himself. The actions themselves can be performed more quickly and with greater resistance to error, thereby reducing the resulting risk of patient/staff injury and material consumption.

For example, this also enables the entry of relevant treatment parameters.

In this way, information interfaces and input interfaces exclusively of the (often only the) parameter(s) relevant for the current treatment step can be visually highlighted by depth effect as state Z1. This is done as an intuitive contrast to the passive/currently irrelevant display and control elements corresponding to a state ZN.

In this way, it can be achieved that more information can be presented on the display DIS without the user orientation during interaction suffering as a result. In particular, an additional context (that of current relevance) is hereby presented, which enables correct operation of the medical device 1 even without understanding the text displays/image symbols, or at least supports this.

In a further embodiment, the first state Z1 is a time with respect to a currently executed process or process step of the medical device 1. Time is to be understood both as lead time, e.g., in the preparation of a treatment, as elapsed time of a process step of the treatment process or as remaining time of a process step of the treatment process, without being limited to this listing.

In one embodiment, the first state Z1 with depth effect is shown on the display DIS, where the depth effect t is dependent on the value of the associated state Z1. The value can be dependent, for example, on a temporal progress of the procedural step of the treatment process, an already achieved (measured) progress, e.g., withdrawal of a certain amount of fluid, the value of a measured physiological variable (e.g., blood pressure) and/or the deviation from a preset value (e.g., deviation to the target blood pressure), etc.

Furthermore, the display 200*a* of the first state Z1 may also serve for user guidance. In particular, displayed interface elements of the display DIS may then also be identical for display and user input with respect to a state. In particular, possible user input may also be limited to interface elements of the display DIS that serve to display 200*a* of the first state Z1, while interface elements of the display DIS that serve to display 200*b* of the second state Z2 do not allow user input.

The medical device also allows user guidance when sequence-independent parameters are entered.

In contrast to e.g., treatment parameters, digital sheets with many individual entries must also be filled in in an interchangeable sequence during device operation, e.g., when entering configuration parameters. Such parameters are usually copied from a template and are entered completely on a single display or in a sequence of individual displays with confirmation of the entries in each case.

This is either confusing (a display) and thus error-prone and time-consuming, or interaction-heavy (thus also time-consuming and error-prone). Input fields can be displayed as states Z1 . . . ZN one after the other (after entering an input it is continued). Optionally, it can be provided that only correspondingly highlighted states Z1 are operable in step 300.

This combines the simultaneous display of all parameters to be entered with the guided input of individual input windows without requiring additional interaction. In addition, the order of the highlighted fields/parameters suggests a consistent template from which to read the values.

This can save input time, reduce the amount of interaction required and avoid input errors, as well as reducing the amount of effort required by staff to operate the system.

Messages without a direct need for action, which recur over time but are not acute, cover at least part of the display on the common displays until they are acknowledged.

The user U may instead be notified of the occurrence of required conditions via a temporally increasing depth display of a corresponding symbol. If the triggering conditions are removed, the corresponding message(s) can be (automatically) moved to the background (state Z2 . . . ZN) or the message(s) can be deleted, i.e., they are no longer displayed.

Alternatively, the user can downgrade the messages (or corresponding icons) back to the background (i.e., the depth display is reduced) before they appear completely in the foreground without having taken care of the causes. This can be understood similar to the "snooze" function of an alarm clock.

This enables the perception of non-acute messages without influencing/interrupting the current display. In terms of patient safety, the course of treatment, etc., more relevant device interactions of the user can thus continue undisturbed and the user decides for himself when to react to less important messages.

In the case of a normal course of treatment, in particular an error-free course of treatment and/or after treatment, the DIS display can be used for a large part of the time as a standby display. In this case, data relevant to the treatment is not displayed primarily for the staff U, but e.g., entertainment media for the patient.

In this embodiment, the autostereographic function of the display DIS can be used to display treatment-relevant monitoring parameters for a user U in a depth-shifted manner simultaneously with the 2D display of, for example, a resting video. This depth effect can be designed in such a way that it is noticeable to a user U, who is at a different distance than a patient from the display DIS, without being perceived as disturbing by the patient.

Without limiting generality, preparatory steps, such as a self-test of functions of the medical device 1, a self-calibration, etc., may be provided in step S0 to put the medical device 1 in a working state for treating a patient.

Further, without limiting the generality, post-processing steps such as checking actuators/sensors, venting, closing valves/openings, emptying collection/storage containers, etc., may be provided in step 800 to place the medical device 1 in an idle state.

Without limiting the generality, medical device 1 may be a dialysis machine.

The medical device 1 may be particularly suitable for renal dialysis, and in particular for at least one of peritoneal dialysis, hemofiltration, hemodiafiltration, or hemoperfusion.

Alternatively, or additionally, the medical device 1 may be suitable for liver dialysis, and in particular for at least one of Apheresis, Single Pass Albumin Dialysis, Molecular Adsorbents Recirculation System.

In some embodiments, it may further be provided that the medical device 1 further provides a display with contactless input. In particular, it may be provided that inputs in step 300 with respect to the first state Z1 can be made without contact.

Here, control elements represented in spatial depth as state Z1 can be triggered without contact by entering the space in which the image appears (in front of the actual display DIS). Additionally, triggering of non-spatially represented elements corresponding to state ZN, e.g., by usual touching of the display DIS, can be excluded.

This is advantageous with regard to hygienic aspects (germ transmission) in the operation of medical devices 1. In addition, a restriction of the readability of the DIS display due to manual contamination is avoided.

Contactless input methods or input devices HID can be based, for example, on radar, lidar, airflow, camera and NFC, without being limited to a specific technology in this respect.

The disclosure solves the present problems by using spatial depth-dependent differentiation in the representation of various elements on the display DIS. The generated display is thus a 3D image, in whose depth property t additional information is integrated in an intuitively understandable way (since it corresponds to the usual perception of spatial, stereoscopic, vision) and at the same time selectively contrasted. For this purpose, use is made directly of the physiology of the human eye, in that the contrasting of the displayed information, corresponding to the different depth representation, takes place selectively through the different focusing within the framework of the accommodation of the eye.

This allows to increase the quantity of information presented on the same area of the display DIS. This also allows prioritizing the display of display elements according to context-dependent relevance. This ensures that despite a large amount of displayed information, the validly perceived information flow remains limited according to the user's capacities.

For the technology to be used for 3D display without additional equipment (i.e., glasses-free), i.e., autostereography, various technologies may come into use for the display DIS.

One possibility is to generate two different images (one for each eye of the viewer) by using beam-splitting display geometry. Alternatively, this can be achieved by integrating lenses and prisms in the display DIS.

Another option is available with the combination of LCD displays and collimation and corresponding (scanning) backlighting.

You can also use a parallax barrier with a subdivision of the display pixels into right/left (with respect to the eyes) subpixels.

In simple implementation, the desired effect can also already be achieved with an overlap of several (transparent) displays (one per depth plane) with separately controllable transmission properties.

The invention claimed is:

1. A method for a medical device having a display and having a processing unit,
the processing unit being suitable for detecting states of one or more technical units of the medical device,
the processing unit furthermore being set up to drive the display on the basis of detected states in order to output states of the medical device, wherein
the display is an autostereographic display, and
the processing unit, based on an evaluation of detected states, drives the display in such a way that a first state is visually highlighted with respect to a 3D representation,
while a second state is visually not highlighted with respect to a 3D representation, the method comprising:
displaying the first state,
displaying the second state, and
receiving user input related to the displayed first state, wherein
the first state is shown on the display with depth effect, the depth effect magnitude being dependent on the value of the associated state.

2. The method of claim 1, further comprising detecting a warning or alarm message, wherein the detected warning or alarm message is displayed as a first state.

3. The method of claim 1, wherein the first state relates to a first step of an operating procedure and the second state relates to a step of the operating procedure subsequent to the first step.

4. The method of claim 1, wherein the first state is a time relating to a currently executed method or method step of the medical device.

5. The method of claim 1, wherein the first state is shown on the display with depth effect, while the second state is shown on the display without depth effect.

6. The method of claim 1, wherein the first state is for user guidance.

7. The method of claim 6, wherein interface elements of the display for display and user input are identical with respect to a state.

8. A medical device having
a display and having a processing unit,
the processing unit being suitable for detecting states of one or more technical units of the medical device,
the processing unit furthermore being set up to drive the display on the basis of detected states in order to output states of the medical device, wherein
the display is an autostereographic display, and
the processing unit, based on an evaluation of detected states, is configured to control the display in such a way that a first state is visually highlighted with respect to a 3D representation, while a second state is not visually highlighted with respect to a 3D representation, wherein
the first state is shown on the display with depth effect, the depth effect magnitude being dependent on the value of the associated state.

9. The medical device of claim 8, wherein the first state relates to a warning or alarm message.

10. The medical device of claim 8, wherein the first state relates to a first step of an operating procedure and the second state relates to a step of the operating procedure subsequent to the first step.

11. The medical device of claim 8, wherein the first state is for user guidance.

12. The medical device of claim 8, wherein the first state is a remaining time of a currently executed method or method step.

13. The medical device of claim 8, wherein the medical device is a dialysis device.

14. The medical device of claim 8, wherein the display is a touch screen.

15. The medical device of claim 8, wherein the second state is shown on the display without depth effect.

16. The medical device of claim 8, wherein the device provides the display with contactless input.

17. The medical device of claim 16, wherein inputs relating to the first state can be made without contact.

* * * * *